US012616688B2

(12) United States Patent
Liu et al.

(10) Patent No.: US 12,616,688 B2
(45) Date of Patent: May 5, 2026

(54) CELL GLYCOCALYX PROTECTION EFFECT OF ANISODAMINE

(71) Applicant: CHENGDU FIRST PHARMACEDTICAL CO., LTD, Chengdu (CN)

(72) Inventors: Zhaohua Liu, Chengdu (CN); Ye Zeng, Chengdu (CN)

(73) Assignee: CHENGDU FIRST PHARMACEDTICAL CO., LTD, Chengdu (CN)

( * ) Notice: Subject to any disclaimer, the term of this patent is extended or adjusted under 35 U.S.C. 154(b) by 497 days.

(21) Appl. No.: 18/024,592

(22) PCT Filed: Sep. 1, 2021

(86) PCT No.: PCT/CN2021/115900

§ 371 (c)(1),
(2) Date: Mar. 3, 2023

(87) PCT Pub. No.: WO2022/048561

PCT Pub. Date: Mar. 10, 2022

(65) Prior Publication Data

US 2023/0321072 A1     Oct. 12, 2023

(30) Foreign Application Priority Data

Sep. 3, 2020    (CN) .......................... 202010914458.3

(51) Int. Cl.
| | |
|---|---|
| C07D 471/08 | (2006.01) |
| A61K 31/439 | (2006.01) |
| A61K 31/46 | (2006.01) |
| A61P 9/00 | (2006.01) |
| A61P 9/14 | (2006.01) |

(52) U.S. Cl.
CPC ................ *A61K 31/46* (2013.01); *A61P 9/14* (2018.01)

(58) Field of Classification Search
CPC .... C07D 471/08; A61K 31/439; A61K 31/46; A61P 9/00; A61P 9/14
See application file for complete search history.

(56) References Cited

FOREIGN PATENT DOCUMENTS

CN            112121047 A     12/2020

OTHER PUBLICATIONS

Du et al., Anisodamine Hydrobromide Protects Glycocalyx and Against the Lipopolysaccharide-Induced Increases in Microvascular Endothelial Layer Permeability and Nitric Oxide Production, vol. 12, No. 1, pp. 91-100 (Year: 2021).*

Sun Jun, et al., Inhibitory effects of anisodamine on lipopolysa••chrides attaching to endothelium and inducing NO release, J Fourth Mil Med Univ, 2001, pp. 1082-1084, vol. 22 No. 12.

Fang Chuan-Biao, et al., Effect of lipopolysaccharide on cytosolic Ca2+ and Gq protein in pulmonary microvascular endothelial cells of rats and the interferring action of anisodamine, Chinese Journal of Pathophysiology, 2002, pp. 454-457, vol. 18 No. 5.

Ruan Qiu-Rong, et al., Anisodamine Downregulates PAI-1 Expression of Cultured Endothelial Cells, Chin J Arterioscler, 2001, pp. 194-197, vol. 9 No. 3, ISSN: 1007-3949.

Mou Yong-Fang, et al., The inhibitory effect of anisodamine on experimental atherosclerosis in rabbits, Chinese Journal of Pathophysiology, 1990, pp. 104-107, vol. 6 No. 2.

Hou Deren, et al., Effects of anisodamine of ICAM-1 expression of cerebral microvascular endothelial cells during hypoxia-reoxygenation, Chin J Crit Care Med, 2003, pp. 127-128, vol. 23 No. 3.

Zhao Xiaojie, Observation on therapeutic effect of anisodamine on ischemic stroke, HeiLongJiang Medicine Journal, 1998, pp. 235-236, vol. 11 No. 4.

Zhang Zhimin, Anisodamine in the treatment of diabetes, 1996, pp. 298, vol. 15 No. 6.

Wen KE, et al., Endothelial glycocalyx and cardiovascular disease, Chinese Pharmacological Bulletin, 2008, pp. 981-984, vol. 24 No. 8.

Kang Hong-Yan, et al., The development of the visualization and measurement techniques of the endothelial glycocalyx, Chinese Bulletin of Life Sciences, 2016, pp. 1089-1099, vol. 28 No. 9.

Ye Shijun, et al., Inhibitive Effect of Anisodamine on Increase of Vascular Permeability after Injection of *Escherichia coli* Endotoxin in Mice, Acia Academiae Medicinae Sinicae, 1988, pp. 439-441, 22-23, vol. 10 No. 6.

Jay M. Poupko, et al., The Pharmacological Properties of Anisodamine, Journal of Applied Toxicology, 2007, pp. 116-121, vol. 27.

* cited by examiner

*Primary Examiner* — Brenda L Coleman

(74) *Attorney, Agent, or Firm* — Bayramoglu Law Offices LLC

(57)                    ABSTRACT

A use of anisodamine or a pharmaceutically acceptable salt thereof in the preparation of a cellular glycocalyx protectant and a use of the anisodamine or the pharmaceutically acceptable salt thereof as a cellular glycocalyx protectant in the restoration and protection of cellular glycocalyx and a cell adhesion junction are provided. The use of the anisodamine or the pharmaceutically acceptable salt thereof in the preparation of cellular glycocalyx protectant also has an effect of protecting the structure and function of an endothelial cell.

12 Claims, 5 Drawing Sheets

CELL GLYCOCALYX PROTECTION EFFECT OF ANISODAMINE

CROSS REFERENCE TO THE RELATED APPLICATIONS

This application is the national phase entry of International Application No. PCT/CN2021/115900, filed on Sep. 1, 2021, which is based upon and claims priority to Chinese Patent Application 202010914458.3, filed on Sep. 3, 2020, the entire contents of which are incorporated herein by reference.

TECHNICAL FIELD

The present disclosure relates to the field of pharmaceuticals, health foods, or foods, and in particular, the present disclosure relates to the restorative and protective effects of anisodamine for endothelial glycocalyx (EG), cadherin, and permeability.

BACKGROUND

Vascular diseases are closely related to endothelial dysfunction. Serum lipopolysaccharides (LPSs) are closely related to atherosclerosis (AS). High-density lipoproteins (HDLs) can bind to LPS. The sharp drop in an HDL level during AS, stroke, and sepsis may lead to a decrease in LPS clearance.

LPS can inhibit the formation of endothelial adhesion junctions by down-regulating the vascular endothelial cadherin (VE-cadherin) in pulmonary endothelial cells, destroying the pulmonary vascular integrity, and aggravating the inflammatory damage. LPS can destroy the endothelium and promote thrombosis. In addition, LPS inhibits the expression of endothelial nitric oxide synthase (eNOS) but induces the expression of inducible nitric oxide synthase (iNOS), thereby increasing the production of endothelial nitric oxide (NO). LPS can reduce a diastolic response of a blood vessel to acetylcholine (ACh) by increasing oxidative stress, thereby causing hepatic endothelial dysfunction. Therefore, the prevention of endothelial cell damage is deemed a promising new therapeutic strategy.

Glycocalyx covers a surface of vascular endothelial cells (VECs) and has a variety of functions. The chemical composition, mechanical properties, and various physiological functions of EG have been widely described. Glycocalyx plays an important role in maintaining the normal functions of a vascular system and is an adhesion barrier for mechanical receptors and sensors, molecular sieves, and circulating cells such as leukocytes and tumor cells. In mouse embryonic stem cell (mESC)-derived endothelial cells, the degradation of glycocalyx heparan sulfate (HS) will inhibit the shear stress-induced expression of cadherin and eNOS. It has also been observed by atomic force microscopy (AFM) that HS plays an important role in the regulation of NO production. The protection of glycocalyx in a microvessel can also maintain the permeability of the microvessel. Currently, drugs related to glycocalyx that can be used to fight against vascular diseases include serum albumin (sphingosine-1 phosphate (S1P)), sulodexide, pentosan polysulfate, wheat germ agglutinin (WGA), rhamnan sulfate (RS), hawthorn extract WSS 1442, or the like. However, there are currently no drugs that can directly act on glycocalyx.

Anisodamine is an active ingredient extracted from the root of *Anisodus tanguticus* (Maxim.) Pascher of the family Solanaceae in China. Since 1965, anisodamine has been used for the clinical treatment of septic shock, microcirculation disorders, organophosphorus poisoning, smooth muscle spasm, and the like.

SUMMARY

The present disclosure discloses a new use of anisodamine for protecting glycocalyx and cadherin of an endothelial cell and inhibiting the LPS-induced endothelial permeability and NO production.

The present disclosure provides a use of anisodamine or a pharmaceutically acceptable salt thereof in the preparation of a cellular glycocalyx protectant.

Preferably, in the use, the cellular glycocalyx protectant is provided to restore and protect cellular glycocalyx.

Preferably, in the use, the restoring and protecting cellular glycocalyx refers to inhibiting a loss of glycocalyx HS and/or increasing a coverage rate of the glycocalyx HS.

Preferably, in the use, the cellular glycocalyx protectant is further provided to restore and protect a cell adhesion junction; and preferably, the restoring and protecting a cell adhesion junction refers to inhibiting a loss of cadherin and/or increasing a coverage rate of cadherin.

Preferably, in the use, the pharmaceutically acceptable salt is one or more selected from the group consisting of a hydrobromide, a hydrochloride, and a sulfate of anisodamine; and preferably, the anisodamine is (Z)-racanisodamine and/or raceanisodamine.

Preferably, in the use, a cell refers to an endothelial cell, and preferably, the endothelial cell is a VEC; and preferably, the endothelial cell is derived from a human, and more preferably, the endothelial cell is a human brain microvascular endothelial cell (HBMVEC).

In addition, in the use, the anisodamine or the pharmaceutically acceptable salt thereof is further able to protect a structure and function of an endothelial cell; and preferably, the protecting a structure and function of an endothelial cell refers to reducing an increase in permeability of the endothelial cell and/or reducing a production of NO of the endothelial cell.

Preferably, in the use, the anisodamine or the pharmaceutically acceptable salt thereof has a variety of effects such as restoring and protecting cellular glycocalyx, restoring and protecting a cell adhesion junction, reducing an increase in permeability of an endothelial cell, or reducing a production of NO of an endothelial cell; and preferably, the cellular glycocalyx protectant is able to restore and protect both EG and a cell adhesion junction and reduce an increase in permeability and a production of NO of an endothelial cell.

In addition, in the use, the anisodamine or the pharmaceutically acceptable salt thereof is further able to promote the proliferation of an endothelial cell.

In addition, in the use, a content of the anisodamine or the pharmaceutically acceptable salt thereof that promotes the proliferation of an endothelial cell is 20 µg/mL or less and preferably 15 µg/mL or less.

In addition, in the use, the anisodamine or the pharmaceutically acceptable salt thereof is further able to inhibit the proliferation of an endothelial cell.

In addition, in the use, a content of the anisodamine or the pharmaceutically acceptable salt thereof that inhibits the proliferation of an endothelial cell is 80 µg/mL or more and preferably 100 µg/mL or more.

Preferably, in the use, the protecting cellular glycocalyx, the protecting a structure and function of an endothelial cell, and/or the promoting or inhibiting the proliferation of an endothelial cell is achieved under an action of an endogenous or exogenous stimulating substance; and preferably, the endogenous or exogenous stimulating substance refers to endotoxin, and more preferably, the endogenous or exogenous stimulating substance refers to LPS.

The present disclosure has discovered that anisodamine at 20 µg/mL can significantly improve the proliferation of an endothelial cell under an action of LPS and anisodamine at 80 µg/mL can significantly inhibit the proliferation of the cell, indicating a bidirectional regulatory effect of anisodamine for the cell proliferation. Anisodamine can restore the LPS-induced shedding of glycocalyx and cadherin and disruption of an adhesion junction. Anisodamine can significantly alleviate the LPS-induced increase in permeability of VEC and production of NO. Therefore, anisodamine is a promising drug for protecting an endothelial cell and glycocalyx and cadherin thereof.

The present disclosure also provides a method for restoring and protecting a cell adhesion junction, reducing an increase in permeability of an endothelial cell, or reducing a production of NO of an endothelial cell in a body of a subject in need, including: administering the anisodamine or the pharmaceutically acceptable salt thereof described above to the subject.

The present disclosure also provides a method for treating a disease mediated by an LPS-induced increase in permeability of a VEC and a production of NO of an endothelial cell in a subject in need, including: administering the anisodamine or the pharmaceutically acceptable salt thereof described above to the subject.

DETAILED DESCRIPTION OF THE EMBODIMENTS

I. Related Definitions

Figure 1:
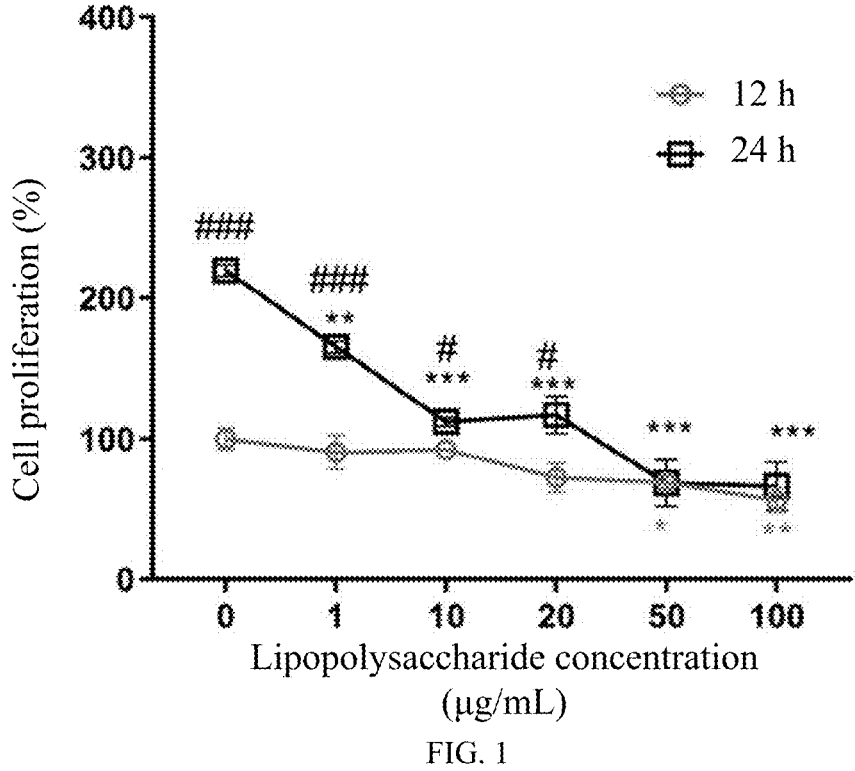
FIG. 1 shows the influence of LPS on the proliferation of an hCMEC/D3 cell, where at a same LPS concentration, *$P<0.05$, $P<0.01$, and *$P<0.001$ vs 0 µg/mL.
Figure 2:
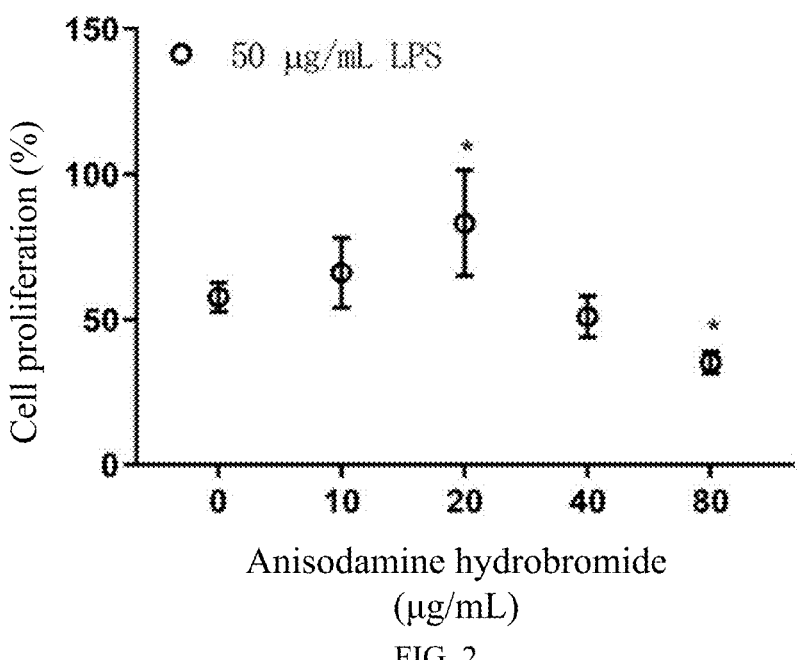
FIG. 2 shows the influence of anisodamine hydrobromide on the proliferation of hCMEC/D3 under an action of LPS, where *$P<0.05$ vs 0 µg/mL anisodamine hydrobromide.

According to the above-mentioned content of the present disclosure, other various forms of modification, substitution, or change can also be made based on the common technical knowledge and conventional means in the art without departing from the above-mentioned basic technical idea of the present disclosure.

Endothelial Cell and a Structure and Function Thereof

The terms "endothelial cell" and "VEC" generally refer to a monolayer of flat epithelium located on an inner surface of a heart, a blood vessel, and a lymphatic vessel, which forms an inner wall of a blood vessel and is an interface between blood in a lumen of a blood vessel and another blood vessel wall (a monolayer of squamous epithelium). Endothelial cells are distributed throughout a circulatory system from the heart to the minimum microvessel, and endothelial cells can devour foreign bodies, bacteria, and necrotic and aged tissues and can also participate in an immune activity function of a body. Endothelial cells can express an adhesion molecule at a high level during inflammation to interact with an adhesion molecule on a surface of a leukocyte in a blood flow, thereby mediating the passage of the leukocyte through a blood vessel wall.

The term "adhesion junction" refers to a main adhesion cell-cell junction in an endothelial cell, which is crucial for the endothelial barrier characteristics and angiogenesis. In many vascular beds, cadherin is a transmembrane chaperone for cytoplasmic catenin, and cadherin stabilizes a junction complex at a cell edge and attaches an adhesion junction to an actin cytoskeleton. Although experimental results regarding the inhibition and de novo synthesis of cadherin are contradictory, the LPS-induced disruption of an endothelial barrier leads to the shedding or intracellular degradation of cadherin. Cadherin is normally continuously distributed around cells, while LPS-induced cadherin is discontinuously distributed around hCMEC/D3 cells.

The loss of heparan sulfate proteoglycan (HSPG) and attached HS will lead to the disruption of a vascular permeability barrier. A shear stress can induce the remodeling of HSPG. The removal of HSPG can eliminate the shear stress-induced expression of cadherin, indicating that the shear stress-induced cadherin plays a role in an HSPG-mediated pathway. The deletion of glycocalyx HSPG can also eliminate the periodic strain-induced transcription of cadherin. Thus, the HS component may be directly involved in vascular permeability and mediate the transcription of cadherin, thereby maintaining the permeability of an endothelial barrier.

The production of NO is a main cause of endothelium-dependent vasodilation and blood pressure drop and is related to diseases such as sepsis, diabetes, AS, shock, and hypertension. Glycocalyx is an important mediator for the production of NO in an endothelial cell. The removal of HSPG with HS can reduce the flow-induced production of NO. Studies have shown that glypican-1 and HS can mediate the fluid shear stress-induced production of NO. Nitric oxide is mainly produced from L-arginine in endothelial cells by calcium/calmodulin-dependent enzymes iNOS and eNOS. LPS induces iNOS and inhibits eNOS. The enhancement of eNOS activity or the supplementation of eNOS can improve the shock outcome. iNOS can not only induce the endothelial dysfunction but also participate in vasoconstriction of sepsis. However, the knockout of an iNOS gene cannot significantly improve a mortality rate of mice undergoing cecal ligation and puncture.

Drug or Pharmaceutical Composition

The anisodamine of the present disclosure, together with one or more auxiliary materials such as adjuvants, a carrier, or a diluent, may be placed in a pharmaceutical composition, a unit dosage, or a dosage form. The pharmaceutical composition may be in a solid dosage form (such as a powder, a granule, a pill, a coated or uncoated tablet, or a filled capsule), a liquid dosage form (such as a solution, a suspension, an emulsion, or a capsule filled thereby), or a semi-solid dosage form (such as a gel, a cream, and an ointment). The dissolution and release properties of one or more active ingredients in the pharmaceutical dosage form can vary in a range from seconds to months.

The "drug" or "pharmaceutical composition" is designed for use in animals and humans and may be administered through any administration route. Preferred administration routes include an injection route, an oral route, a pulmonary route, a nasal route, a rectal route, and a parenteral route. Such a pharmaceutical composition and a unit dosage form thereof may include a conventional or new ingredient in a conventional or special proportion, and may or may not include an additional active compound or ingredient; and such a unit dosage form may include any suitable effective amount of an active ingredient to be adopted commensurate with a target daily dose range.

The term "carrier" used for the pharmaceutical composition of the present disclosure relates to a diluent, an auxiliary material, or an excipient administered together with the active compound.

Therapeutic Method and Drug Formulation

Through an oral route, an injection route, a rectal route, or a parenteral route (including an intravenous route and a subcutaneous route) or in some cases even through a local route, the active ingredient shown in formula I of the present disclosure may be administered alone or may be administered in conjunction with one or more drugs (an acceptable auxiliary material, a carrier, or a diluent, particularly and preferably in the form of a pharmaceutical composition thereof) at an effective amount to a subject in need such as a live animal (including a human) to treat, relieve or improve, and alleviate or eliminate indications or diseases to which the active ingredient is sensitive or indications or diseases described elsewhere in the present disclosure.

As used herein, the term "treatment" refers to relieving or alleviating at least one symptom of a disease in a subject; and within the meaning of the present disclosure, the term "treatment" also refers to inhibiting and delaying an onset (namely, pre-clinical manifestations of a disease) and/or reducing a risk of developing or worsening a disease.

As used herein, the term "restoration" means that, when a function and/or structure of a cell change(s) under an action of a specific endogenous or exogenous stimulating substance such as endotoxin and a structural abnormality and/or a functional abnormality occur(s), an abnormal state is returned to a normal state. The term "protection" refers to reducing or avoiding the further alteration or damage by the endogenous or exogenous stimulating substance to a structure and/or function of a cell.

The drug or pharmaceutical composition of the present disclosure may be administered orally, locally, parenterally, or mucosally (such as buccally, through inhalation, or rectally) in a dosage unit formulation including a conventional non-toxic pharmaceutically acceptable carrier. The oral route is usually desired. The active reagent may be administered orally in a form such as a capsule or a tablet (as shown in Remington: The Science and Practice of Pharmacy, 20th Edition).

For oral administration in a tablet or capsule form, the active pharmaceutical ingredient may be used in combination with a non-toxic, pharmaceutically acceptable auxiliary material such as a binder (such as pre-gelatinized cornstarch, polyvinylpyrrolidone (PVP), or hydroxypropyl methylcellulose (HPMC)); a filler (such as reducing and non-reducing sugars such as lactose, sucrose, glucose, mannitol, and sorbitol, microcrystalline cellulose (MCC), calcium sulfate, or dicalcium phosphate (DCP)); a lubricant (such as magnesium stearate, talcum powder or silicon earth, stearic acid, sodium stearyl fumarate, glyceryl behenate, and calcium stearate); a disintegrating agent (such as potato starch or sodium starch glycolate); or a wetting agent (such as sodium lauryl sulfate (SLS)), a coloring agent and a flavoring agent, gelatin, a sweetener, a natural and synthetic gum (such as arabic gum, tragacanth gum, or alginate), a buffer salt, carboxymethylcellulose (CMC), polyethylene glycol (PEG), wax, or the like. For oral administration in a liquid form, the pharmaceutical ingredient may be used in combination with a non-toxic, pharmaceutically acceptable inert carrier (such as ethanol, glycerin, and water), an anti-settling agent (such as a sorbitol solution, a cellulose derivative, or a hydrogenated edible fat), an emulsifying agent (such as lecithin or arabic gum), a non-aqueous carrier (such as almond oil, an oil ester, ethanol, or a fractionated vegetable oil), a preserving agent (such as methyl p-hydroxybenzoate, propyl p-hydroxybenzoate, or sorbic acid), or the like. A stabilizer such as an antioxidant (BHA, BHT, propyl gallate (PG), sodium ascorbate, or citric acid) may also be added to stabilize the dosage form.

A tablet including the active compound may be coated by a method well known in the art. The composition of the present disclosure including a compound shown in formula I as an active compound may also be introduced into a bead, a microsphere, or a microcapsule, which is constructed from polyglycolic acid (PGA)/lactic acid (PGLA), for example. A liquid formulation for oral administration may be, for example, in a form of a solution, a syrup, an emulsion, or a suspension, or may be presented as a dry product that needs to be reconstructed with water or another suitable auxiliary material before use. A formulation for oral administration may be appropriately prepared to allow the controlled or delayed release of the active compound.

The drug or pharmaceutical composition of the present disclosure may be delivered parenterally, namely, intravenously (i.v.), intraventricularly (i.c.v.), subcutaneously (s.c.), intraperitoneally (i.p.), intramuscularly (i.m.), subcutaneously (s.d.), or intracutaneously (i.d.); and the drug or pharmaceutical composition may be directly injected, for example, through rapid injection or continuous infusion. A formulation for injection may be presented in a unit dosage form, for example, the formulation may be placed in an ampoule or a multi-dose container with a preserving agent. The composition may be in a shape of an excipient or in a form of a suspension, solution, or emulsion in an oil or aqueous carrier, and may include a formulation reagent such as an anti-settling agent, a stabilizer, and/or a dispersing agent. Alternatively, the active ingredient may be in a powder form that needs to be reconstructed with a suitable carrier (such as sterile pyrogen-free water) before use.

The drug or pharmaceutical composition of the present disclosure may also be prepared for rectal administration, such as a suppository or a retention enema (for example, including a conventional suppository base such as cocoa butter or another glyceride).

II. Specific Embodiments

The present disclosure is further illustrated below with reference to embodiments. The descriptions of specific exemplary embodiments of the present disclosure are presented for purposes of illustration and exemplification. These descriptions are not intended to limit the present disclosure to the precise forms disclosed, and obviously, many modifications and variations may be made in light of teachings of the specification of the present disclosure. The exemplary embodiments are selected and described to explain the specific principle of the present disclosure and a practical application thereof, such that a person skilled in the art can make and utilize various different exemplary embodiments of the present disclosure and various different options and modifications.

An aspect of the present disclosure relates to a use of anisodamine or a pharmaceutically acceptable salt thereof in the preparation of a cellular glycocalyx protectant.

Preferably, the present disclosure relates to a use of the anisodamine or the pharmaceutically acceptable salt thereof in the preparation of a drug for restoring and protecting cellular glycocalyx; and preferably, the restoring and protecting cellular glycocalyx refers to inhibiting a loss of glycocalyx HS and/or increasing a coverage rate of the glycocalyx HS.

Preferably, the present disclosure relates to a use of the anisodamine or the pharmaceutically acceptable salt thereof in the preparation of a drug for restoring and protecting a cell adhesion junction; and preferably, the restoring and protecting a cell adhesion junction refers to inhibiting a loss of cadherin and/or increasing a coverage rate of cadherin.

Preferably, the pharmaceutically acceptable salt of the anisodamine is one or more selected from the group consisting of a hydrobromide, a hydrochloride, and a sulfate of anisodamine.

Preferably, the anisodamine is (Z)-racanisodamine and/or raceanisodamine.

Preferably, a cell refers to an endothelial cell, and preferably, the endothelial cell is a VEC; and preferably, the endothelial cell is derived from a human, and more preferably, the endothelial cell is an HBMVEC.

The present disclosure also relates to a use of the anisodamine or the pharmaceutically acceptable salt thereof in the preparation of a drug for protecting a structure and function of an endothelial cell; and preferably, the protecting a structure and function of an endothelial cell refers to reducing an increase in permeability of the endothelial cell and/or reducing a production of NO of the endothelial cell.

Preferably, the present disclosure also relates to a use of the anisodamine or the pharmaceutically acceptable salt thereof in the preparation of a drug with one or more functions selected from the group consisting of the following functions: restoring and protecting cellular glycocalyx, restoring and protecting a cell adhesion junction, reducing an increase in permeability of an endothelial cell, and reducing a production of NO of an endothelial cell; and preferably, the drug is a cellular glycocalyx protectant, and the cellular glycocalyx protectant is able to restore and protect both EG and a cell adhesion junction and reduce an increase in permeability and a production of NO of an endothelial cell.

The present disclosure also relates to a use of the anisodamine or the pharmaceutically acceptable salt thereof in the preparation of a drug for promoting the proliferation of an endothelial cell.

In an aspect of the present disclosure, a content of the anisodamine or the pharmaceutically acceptable salt thereof that promotes the proliferation of an endothelial cell is 20 µg/mL or less and preferably 15 µg/mL or less.

The present disclosure also relates to a use of the anisodamine or the pharmaceutically acceptable salt thereof in the preparation of a drug for inhibiting the proliferation of an endothelial cell.

In an aspect of the present disclosure, a content of the anisodamine or the pharmaceutically acceptable salt thereof that inhibits the proliferation of an endothelial cell is 80 µg/mL or more and preferably 100 µg/mL or more.

An aspect of the present disclosure relates to a role of the anisodamine or the pharmaceutically acceptable salt thereof to protect cellular glycocalyx, protect a structure and function of an endothelial cell, and/or promote or inhibit the proliferation of an endothelial cell under an endogenous or exogenous stimulating substance; and preferably, the endogenous or exogenous stimulating substance refers to endotoxin, and more preferably, the endogenous or exogenous stimulating substance refers to LPS.

Preferably, the anisodamine or the pharmaceutically acceptable salt thereof in the present disclosure has restorative and protective effects for the endogenous or exogenous stimulating substance (such as LPS)-induced shedding of glycocalyx, and/or has restorative and protective effects for the endogenous or exogenous stimulating substance (such as LPS)-induced disruption of an adhesion junction, and/or alleviates the endogenous or exogenous stimulating substance (such as LPS)-induced endothelial permeability, and/or reduces the endogenous or exogenous stimulating substance (such as LPS)-induced NO production of an endothelial cell.

Preferably, an action concentration of the anisodamine is less than 80 µg/mL, or less than 70 µg/mL, or less than 60 µg/mL, or less than 50 µg/mL, or less than 40 µg/mL, or less than 30 µg/mL, or less than 20 µg/mL, or less than 10 µg/mL, or 2 µg/mL to 50 µg/mL, preferably 5 µg/mL to 25 µg/mL, more preferably 10 µg/mL or 20 µg/mL, and most preferably 10 µg/mL or 20 µg/mL; and preferably, the action concentration refers to a concentration at which the drug directly acts on a cell.

Preferably, the endothelial cell is derived from a human, and more preferably, the endothelial cell is an HBMVEC.

The present disclosure also provides a method for restoring and/or protecting cellular glycocalyx, including: administering the anisodamine or the pharmaceutically acceptable salt thereof described above to a subject.

Preferably, the restoring and protecting cellular glycocalyx refers to inhibiting a loss of glycocalyx HS and/or increasing a coverage rate of the glycocalyx HS.

The present disclosure also provides a method for restoring and protecting a cell adhesion junction, including: administering the anisodamine or the pharmaceutically acceptable salt thereof described above to a subject.

Preferably, the restoring and protecting a cell adhesion junction refers to inhibiting a loss of cadherin and/or increasing a coverage rate of cadherin.

The present disclosure also provides a method for protecting a structure and function of an endothelial cell; and preferably, the protecting a structure and function of an endothelial cell refers to reducing an increase in permeability of the endothelial cell and/or reducing a production of NO of the endothelial cell.

Preferably, the cell is an endothelial cell and preferably a VEC.

Preferably, the endothelial cell is derived from a human or another animal, and more preferably, the endothelial cell is an HBMVEC.

In an aspect, the present disclosure provides a method for restoring and protecting a cell adhesion junction in a body of a subject in need, including: administering the anisodamine or the pharmaceutically acceptable salt thereof described above to the subject.

In an aspect, the present disclosure provides a method for reducing an increase in permeability of an endothelial cell in a body of a subject in need, including: administering the anisodamine or the pharmaceutically acceptable salt thereof described above to the subject.

In an aspect, the present disclosure provides a method for reducing a production of NO of an endothelial cell in a body of a subject in need, including: administering the anisodamine or the pharmaceutically acceptable salt thereof described above to the subject.

In an aspect, the present disclosure provides a method for treating a disease mediated by an LPS-induced increase in permeability of a VEC in a subject in need, including: administering the anisodamine or the pharmaceutically acceptable salt thereof described above to the subject.

In an aspect, the present disclosure provides a method for treating a disease mediated by a production of NO of an endothelial cell in a subject in need, including: administering the anisodamine or the pharmaceutically acceptable salt thereof described above to the subject.

Preferably, the protecting cellular glycocalyx, the protecting a structure and function of an endothelial cell, and/or the promoting or inhibiting the proliferation of an endothelial cell is achieved under an action of an endogenous or exogenous stimulating substance.

Preferably, the endogenous or exogenous stimulating substance refers to endotoxin.

Preferably, the endogenous or exogenous stimulating substance refers to LPS.

III. Examples

Example 1 Influence of Anisodamine Hydrobromide on the LPS-Induced Proliferation of a hCMEC/D3 Cell 1.1 Cell Cultivation and Treatment Immortalized HBMVEC hCMEC/D3 was taken from the Beijing Beina Chuanglian Biotechnology Institute (BNBIO) in China. The hCMEC/D3 endothelial cell was cultivated with an endothelial cell culture medium (ECM; cat.1001, Sciencell, USA) at 37° C. and 5% $CO_2$. Anisodamine hydrobromide was taken from the Chengdu First Pharmaceutical Co., Ltd., Chengdu, China. Anisodamine hydrobromide was dissolved in distilled water at 20 mg/mL, then a resulting solution was filtered through a 0.22 μm filter membrane, and anisodamine hydrobromide solutions with final concentrations of 10 μg/mL, 20 μg/mL, 40 μg/mL, and 80 μg/mL each were prepared with ECM. LPS was dissolved in distilled water at 2 mg/mL, and LPS solutions with concentrations of 1 μg/mL, 10 μg/mL, 20 μg/mL, 50 μg/mL, and 100 μg/mL each were prepared with ECM. The hCMEC/D3 cell was treated with LPS and anisodamine hydrobromide.

1.2 Cell Proliferation Assay

The cell proliferation was assayed by the CCK-8 method (C0042, Beyotime, China). 2,000 cells were inoculated into a 96-well plate, cultivated for 24 h, and then treated with LPS and anisodamine hydrobromide; and before the end of the experiment, a CCK8 assay solution was added, the plate was incubated for 1 h, and then the absorbance at 450 nm was determined by a microplate reader (Labsery K3 Touch, Thermo Fisher, USA).

1.3 Results

The CCK-8 method was used to assay the cell proliferation at 12 h and 24 h after the action of LPS (1 μg/mL to 100 μg/mL) on hCMEC/D3. Results showed that LPS of 50 μg/mL and 100 μg/mL significantly inhibited the cell proliferation at 12 h; at 24 h, LPS significantly inhibited the cell proliferation in a concentration-dependent manner; and when an LPS concentration was 50 μg/mL to 100 m/mL, there was no significant change in cell proliferation from 12 h to 24 h. Thus, in the subsequent experiment, the hCMEC/D3 cell was stimulated with 50 μg/mL of LPS for 24 h.

Under 50 μg/mL LPS, anisodamine hydrobromide at 10 μg/mL to 80 μg/mL was added to treat the cell for 24 h. In the presence of LPS, anisodamine hydrobromide of 20 μg/mL significantly increased the cell proliferation, and anisodamine hydrobromide of 80 μg/mL significantly down-regulated the cell proliferation, indicating that anisodamine hydrobromide has a bidirectional regulatory effect on the proliferation of the hCMEC/D3 cell. Therefore, it can be seen that the action of 20 μg/mL anisodamine hydrobromide for 24 h can protect the hCMEC/D3 cell.

Example 2 Influence of Anisodamine Hydrobromide on Glycocalyx and an Adhesion Junction of VEC 2.1 Experimental Groups: Normal Control Group, LPS Treatment Group (50 μg/mL), Low-Concentration Administration Group (LPS 50 μg/mL+Anisodamine Hydrobromide 10 μg/mL), and High-Concentration Administration Group (LPS 50 μg/mL+Anisodamine Hydrobromide 20 μg/mL).

2.2 Immunofluorescence Staining and Confocal Microscopy

A cell was fixed and penetrated, then blocked with 2% goat serum, and labeled with a murine HS monoclonal antibody (mAb) (1:100, 10E4 epitope, AMS Biotechnology, UK), a rabbit cadherin polyclonal antibody (pAb) (1:100, A0734, Abclonal, China), an Alexa Fluor 488 goat anti-murine (1:400, A11001, Thermo Fisher) secondary antibody, and an Alexa Fluor 568 donkey anti-rabbit (1:400, A10042, Thermo Fisher) secondary antibody. The cell nucleus was labeled with DAPI. Mounting was conducted, and then the cell was detected under a confocal microscope at LSM710.

2.2 Results

Figure 3A:
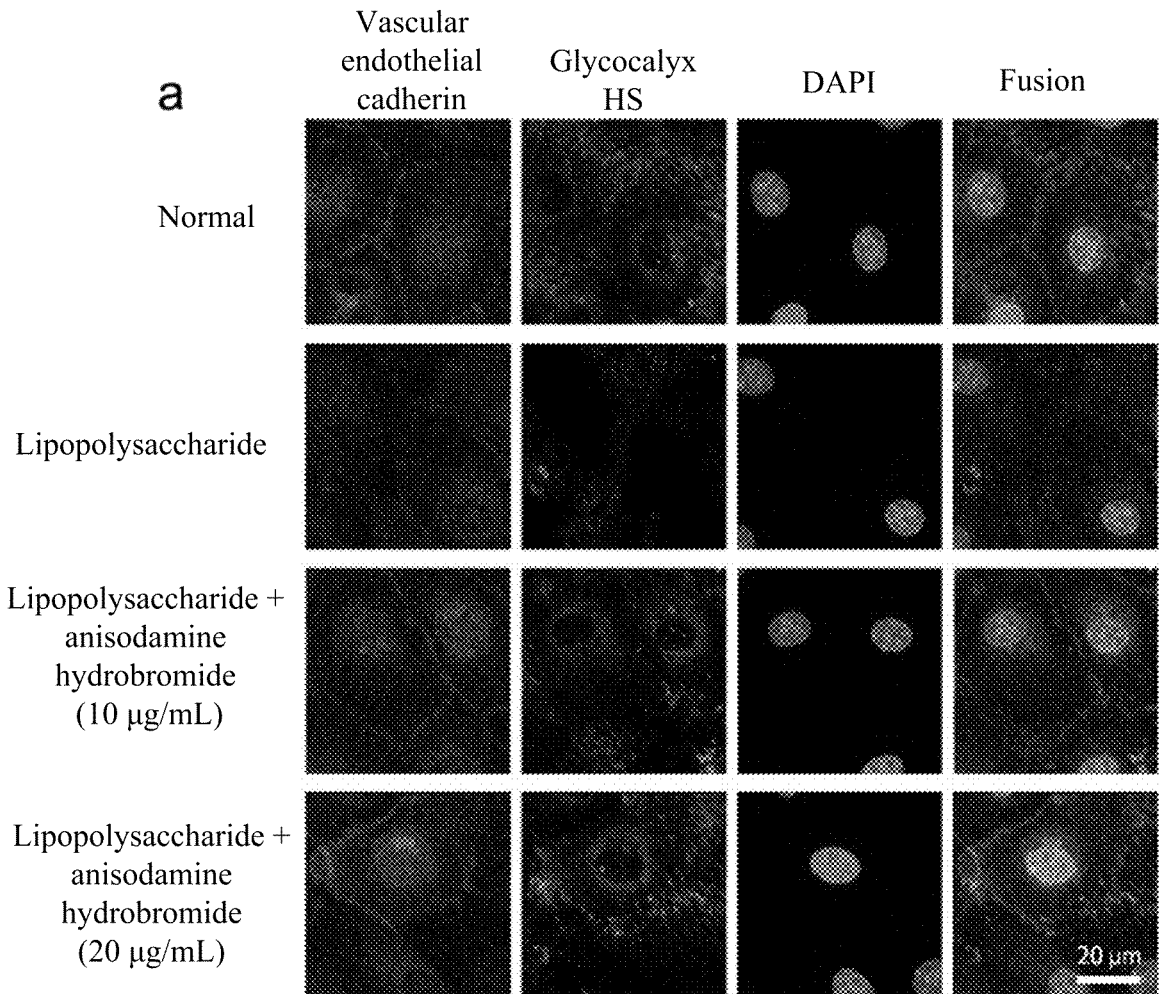
FIG. 3A shows that anisodamine hydrobromide maintains a barrier function of an endothelial cell by protecting glycocalyx and a cell junction (images acquired by confocal microscopy).
Figures 3B, 3C, 3D, 3E:
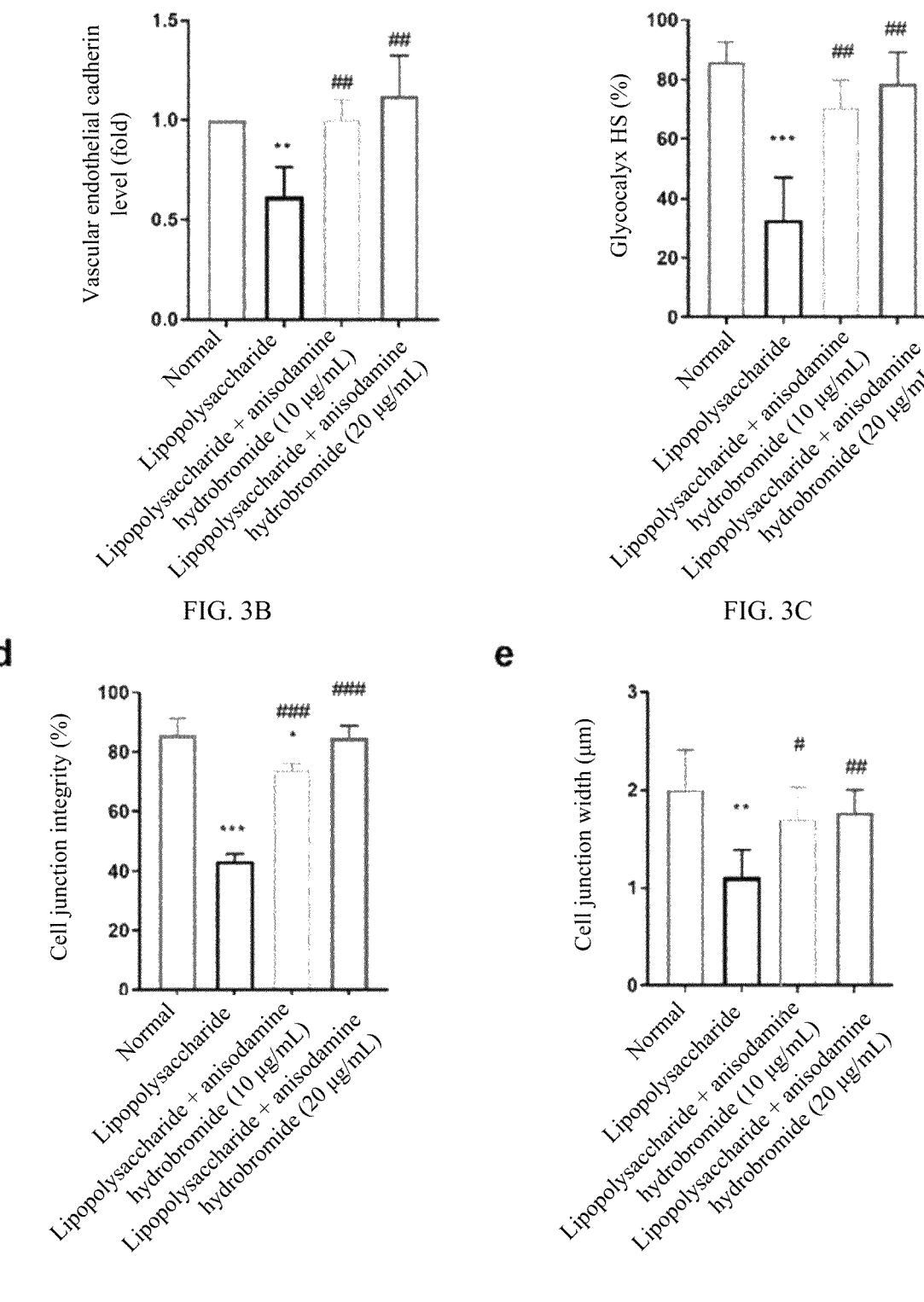
FIGS. 3B-3E show that anisodamine hydrobromide maintains a barrier function of an endothelial cell by protecting glycocalyx and a cell junction (quantification of observation results of confocal microscopy).

Results of the distribution of cadherin and HS observed under a confocal microscope showed that, after the LPS treatment, the cadherin and HS on a surface of the hCMEC/D3 cell lost (FIG. 3A); anisodamine hydrobromide of both 10 μg/mL and 20 μg/mL could inhibit the loss of cadherin and HS (FIG. 3A, and FIGS. 3B-3C); compared with the control group and the 10 μg/mL anisodamine hydrobromide group, the cadherin level and the HS coverage rate increased slightly, but not significantly (FIGS. 3B-3C); after the LPS treatment, a cell junction structure was unclear (FIG. 3A); and anisodamine hydrobromide restored the integrity and width of a cell junction (FIGS. 3D-3E). These results showed that anisodamine hydrobromide had restorative and protective effects for the LPS-induced shedding of glycocalyx and also had restorative and protective effects for the LPS-destroyed adhesion junction.

Example 3 Influence of Anisodamine Hydrobromide on the LPS-Destroyed Endothelial Permeability 3.1 Experimental Groups: Which were the Same as in Example 2.

3.2 Endothelial Permeability Assay

A cell ($5 \times 10^4$ in 200 μL ECM) was inoculated into an upper well of Transwell (0.4 μm, Corning, USA), and 200 μL of ECM was added to a lower well; the Transwell was incubated for 3 d in a 37° C. and 5% $CO_2$ incubator until a cell confluency was 90%; a medium in the upper well was replaced with 50 μg/mL LPS or anisodamine hydrobromide (10 μg/mL or 20 μg/mL)-free fresh ECM, and a medium in the lower well was replaced with fresh ECM; 24 h later, 10

11 | 12

μL of fluorescein isothiocyanate (FITC)-dextran (40 kDa; Cat. 46944, Sigma-Aldrich, USA) was added to the upper well; 40 min later, 100 μL of a medium was taken from the lower well, and fluorescence values at 490 nm and 525 nm were determined; and a leakage amount of FITC-dextran was calculated to assess the permeability of an endothelial cell layer.

3.2 Results

Figure 4:
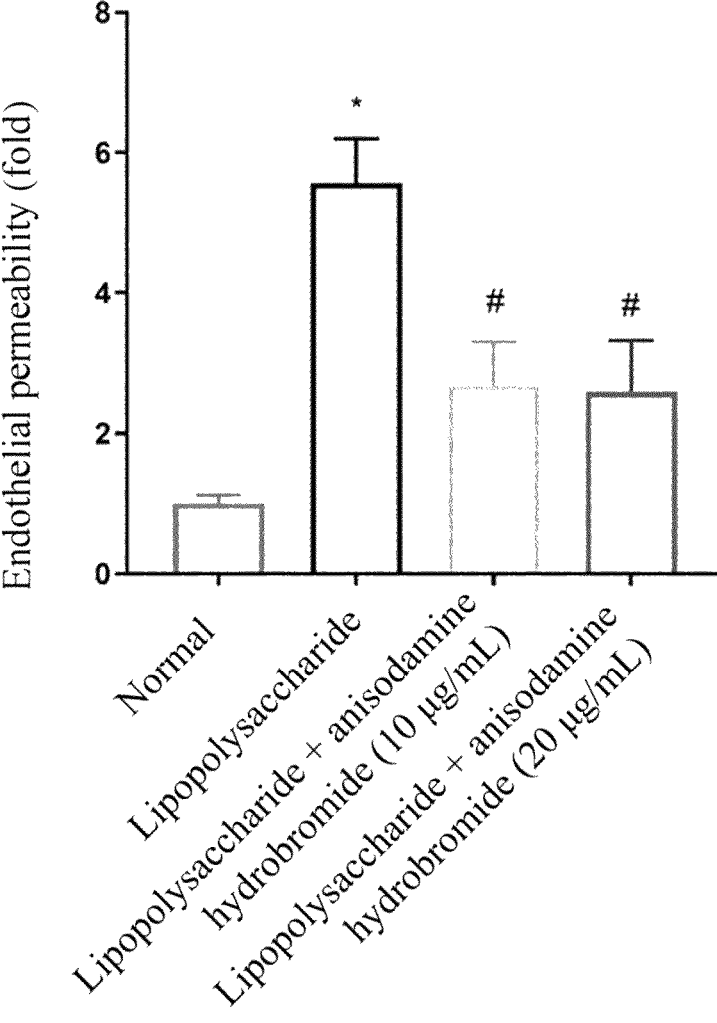
FIG. 4 shows the influence of anisodamine hydrobromide on the endothelial permeability under an action of LPS.

LPS significantly induced a 5.7-fold increase in the permeability of an hCMEC/D3 barrier (FIG. 4). Anisodamine hydrobromide of 10 μg/mL and 20 μg/mL reduced the LPS-induced permeability to 2.7 and 2.6 times of the permeability of the control group, respectively. However, there was no significant difference between the anisodamine hydrobromide group and the control group. Thus, anisodamine hydrobromide alleviated the LPS-induced endothelial permeability.

Example 4 Influence of Anisodamine
Hydrobromide on the LPS-Induced NO Production 4.1 Experimental Groups: Which were the Same as in Example 2.

4.2 NO Production Assay

A cell was pre-cooled with PBS, then ultrasonically disrupted and homogenized, and centrifuged at 16,000 g and 4° C. for 20 min, a resulting supernatant was collected, and a NO detection kit (Nanjing Jiancheng Institute of Biological Engineering A012) was used to determine the absorbance at 550 nm, thereby determining an NO level.

4.3 Results

Figure 5:
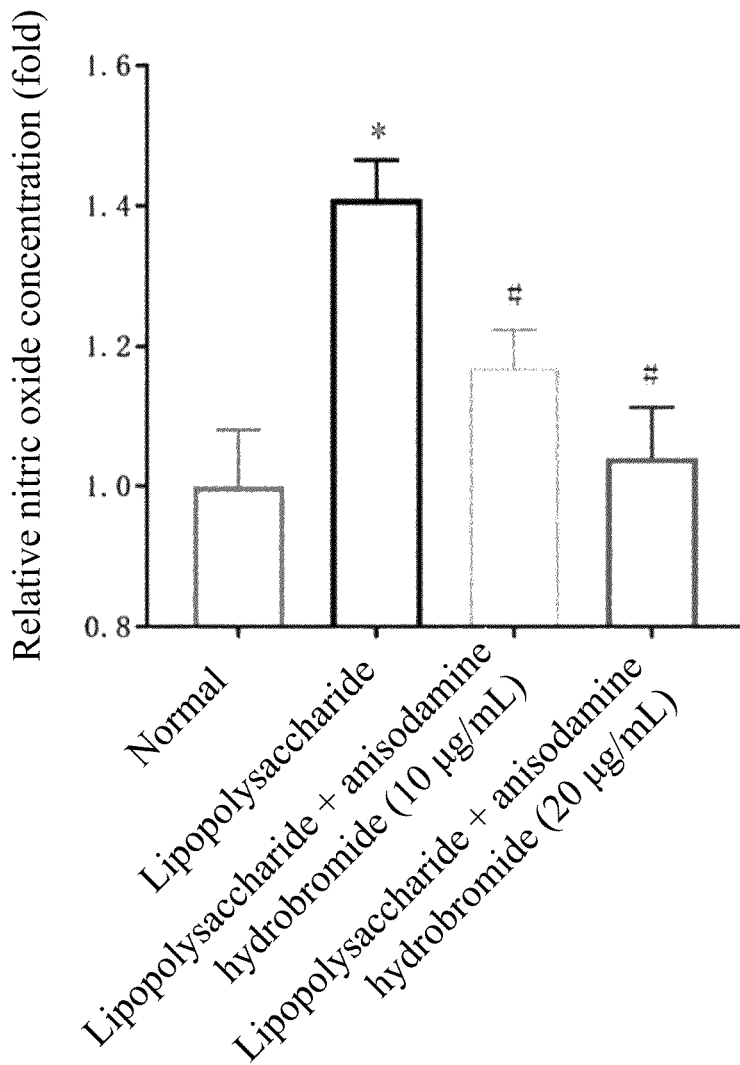
FIG. 5 shows the influence of anisodamine hydrobromide on the LPS-induced production of NO in an hCMEC/D3 cell.

NO assay results showed that LPS significantly induced a 1.4-fold increase in NO production of the hCMEC/D3 cell compared with the control group (FIG. 5); anisodamine hydrobromide of 10 μg/mL significantly reduced the LPS-induced NO production to 1.2 times an NO production of the control group; and anisodamine hydrobromide of 10 μg/mL significantly reduced the LPS-induced NO level, indicating that anisodamine hydrobromide can eliminate the LPS-induced NO production of an endothelial cell.

In the present disclosure, a one-way analysis of variance (ANOVA) test or a t-test was conducted by SPSS software, and $P<0.05$ indicated that a difference was statistically significant.

What is claimed is:

1. A method of restoring and protecting a cellular glycocalyx of a subject in need, comprising administering an effective amount of a cellular glycocalyx protectant, wherein the cellular glycocalyx protectant comprises an anisodamine or a pharmaceutically acceptable salt thereof;

and the restoring and protecting the cellular glycocalyx refers to inhibiting a loss of glycocalyx heparan sulfate and/or increasing a coverage rate of the glycocalyx heparan sulfate, and inhibiting a loss of cadherin and/or increasing a coverage rate of the cadherin.

2. The method according to claim 1, wherein the pharmaceutically acceptable salt is one or more selected from the group consisting of a hydrobromide, a hydrochloride, and a sulfate of the anisodamine; and the anisodamine is (Z)-racanisodamine and/or raceanisodamine.

3. The method according to claim 1, wherein the cellular glycocalyx is that of an endothelial cell, and the endothelial cell is a human brain microvascular endothelial cell.

4. The method according to claim 1, wherein the anisodamine or the pharmaceutically acceptable salt thereof is further able to protect a structure and a function of an endothelial cell; and the protecting the structure and the function of the endothelial cell refers to reducing an increase in a permeability of the endothelial cell and/or reducing a production of nitric oxide (NO) of the endothelial cell.

5. The method according to claim 1, wherein the anisodamine or the pharmaceutically acceptable salt thereof has a plurality of effects comprising restoring and protecting cellular glycocalyx, restoring and protecting a cell adhesion junction, reducing an increase in a permeability of an endothelial cell, or reducing a production of NO of an endothelial cell; and the cellular glycocalyx protectant is able to simultaneously restore and protect endothelial glycocalyx and the cell adhesion junction and reduce the increase in the permeability and the production of the NO of the endothelial cell.

6. The method according to claim 1, wherein the anisodamine or the pharmaceutically acceptable salt thereof is further able to promote a proliferation of an endothelial cell.

7. The method according to claim 1, wherein protecting cellular glycocalyx, protecting a structure and a function of an endothelial cell, and/or promoting a proliferation of the endothelial cell is achieved under an action of a lipopolysaccharide.

8. A method for restoring and protecting a cell adhesion junction, reducing an increase in a permeability of an endothelial cell, or reducing a production of NO of the endothelial cell in a body of a subject in need, comprising: administering the anisodamine or the pharmaceutically acceptable salt thereof according to claim 1 to the subject.

9. The method according to claim 2, wherein the cellular glycocalyx is that of an endothelial cell, and the endothelial cell is a human brain microvascular endothelial cell.

10. The method according to claim 2, wherein the anisodamine or the pharmaceutically acceptable salt thereof is able to protect a structure and a function of an endothelial cell; and the protecting the structure and the function of the endothelial cell refers to reducing an increase in a permeability of the endothelial cell and/or reducing a production of NO of the endothelial cell.

11. The method according to claim 1, wherein the cellular glycocalyx protectant comprises anisodamine hydrobromide.

12. The method according to claim 11, wherein a concentration of the anisodamine that directly acts on a cell is 5 μg/mL to 25 μg/mL.

* * * * *